United States Patent [19]
Addington et al.

[11] Patent Number: 6,004,268
[45] Date of Patent: Dec. 21, 1999

[54] ASPIRATION SCREENING PROCESS FOR ASSESSING POST SURGERY PATIENT'S RISK FOR PNEUMONIA

[76] Inventors: W. Robert Addington, 118 Tradewinds Terrace, Indialantic, Fla. 32903; Robert E. Stephens, 5224 N.W. Bluff Dr., Parkville, Mo. 64152

[21] Appl. No.: 09/064,028

[22] Filed: Apr. 21, 1998

[51] Int. Cl.$^6$ ........................................ A61B 5/00
[52] U.S. Cl. ........................ 600/300; 600/529; 128/898
[58] Field of Search ................................. 600/300, 529, 600/533, 538; 128/898

[56] References Cited

PUBLICATIONS

Florida Hospital Association 1996—"Cost of Dysphagia Testing and treatment of Aspirating Pneumonia." (single sheet) dated Sep. 24, 1997.
Merck Index. 12th ed. 1996 "Tartaric Acid", p. 1552.
United States Department of Labor, Occupational Safety and Health Administration. material Safety Data Sheet (MSDS) on Tartaric Acid (2 sheets).
Addendum to MSDS on Tartaric Acid. "Regulatory Status" (6 sheets).
Partial Listing of OTC Inhalers with Bitartrate. (Single Sheet).
Patty's Industrial Hygiene and Toxicology Vol. 2C 1982 "Tartaric Acid" pp. 4937,4743–5, 4981–2.
Chasseaud LF, Down WH, Kirkpatrick D. 1977 Absorption and Biotransformation of L(+)–Tartaric Acid in Rats. Experientia 33:998–1003.
Fassett DW. Organic Acids, Anhydrides, Lactones, Acid Halides and Amides, Thioacids in Industrial Hygiene and Toxicology 2nd ed. vol. II. DW Fassett and DD Irish, eds., Wiley–Interscience, New York. 1963. pp. 1771–7, 1811, 1814.
Fithugh OG, Nelson AA. 1947 The Comparative Chronic Toxicities of Fumaric, Tartaric, Oxalic and Maleic Acids. J AM Pharm Assocs 36:217–9.
Horn HJ, Holland EG, Hazleton LW. 1957 Safety of Adipic Acid as Compared with Citric and Tartaric Acid. J Agric Food Chem 5:759–61.
Lewis JD. 1977 Comparison of the Distribution of L(+) and DL–Forms of Tartaric Acid in the Rat. Acta Pharmacol Toxicol 41:144–5.
Locke A, Locke RB, Schlesinger H, Carr H. 1942 The Comparative Toxicity and Cathartic Efficiency of Disodium Tartrate and Fumarate, and Magnesium Fumarate for the Mouse and Rabbit, J AM Pharm Assoc 31;12–14.
Smyth Jr. HF, Carpenter CO, Weill CS, Pozzani UC, Striegel JA. 1962 Range–Finding Toxiicity Data: List VI. Am Ind. Hyg. ASsoc J23:95–107.
Sourkes TL, Koppanyi T. Correlation Between the Acute Toxicity and the Rate of Elimination of Tartaric Acid and Certain of its Esters 1950. J AM Pharm Assoc. 39:275–6.
Underhill FP, Leonard CS, Gross EG, Jaleski, TC. 1931. Studies on the Metabolism of Tartrates: II The Behavior of Tartrate in the Organism of the Rabbit, Dog, Rat and Guinea Pig. J Pharmacol 43:359–80.
Weiss JM, Downs CR, Corson HP. 1923 Inactive Malic Acid as a Food Acidulent. Ind Eng Chem 15:628–30. Also cited by Registry of Toxic Effects of Chemical Substances, NIOSH ed., 1978.

(List continued on next page.)

*Primary Examiner*—Eric F. Winakur
*Attorney, Agent, or Firm*—Charles E. Wands

[57] ABSTRACT

Whether a post surgery intubated patient is at risk for aspiration-based pneumonia is determined by requiring the patient to inhale an aerosol of tartaric acid that will stimulate a sensory innervation of the patient's larynx, if functionally recovered, thereby causing the patient to cough. The resulting cough or lack of cough is graded to determine whether the patient is at risk for pneumonia caused by the aspiration of matter present in the patient's mouth. In a further embodiment, the inability or difficulty of a patient to voluntarily expel potentially threatening fluid and matter from the patient's airway can be remedied by repeated applications of the aerosol chemostimulant spray.

9 Claims, 1 Drawing Sheet

OTHER PUBLICATIONS

Who Food Additives Series, No. 5, "Toxicological Evaluation of Some Food Additives Including Anticaking Agents, Antimocrobials, Antioxidants, Emulsifiers and Thickening Agents." [17th Report of the Joint FAO/Who Expert Committee on Food Additives, SHO Technical Report Series, 1974, No. 539; FAO Nutrition Meetings Report Series, 1974, No. 53] Geneva. pp. 14, 222–4, 236–7, 512–4.

Addington WR, Stephens RE, Ockey RR, Kann D, Rodriguez M. A New Aspiration Screening Test to Assess the Need for Modified Barium Swallow Study. Archives of Physical Medicine and Rehabilitation Nov. 1995:76(11):1040.

Addington WR, Stephens RE, Gilliland K, Miller SP. The Laryngeal Evoked Potential (LEP) and Laryngeal Cough Reflex, Muscle and Nerve, Aug. 1997; 20(3); 1071–1072.447.

Alberts MJ, Horner J, Gray L. Brazer SR. Aspiration After Stroke: Lesion analysis by Brain MRI. Dysphagia. 7(3):170–3, 1992.

Alessi DM, Berci G. Aspiration and Nasogastric Intubation. Otolaryngology—Head and Neck Surgery. 94(4):486–9, Apr. 1986.

Aubert M, Guilhen C. Topographie des Projections de la Sensibilite Viscerale Sur L'ecorce Cerebrale du Chat. 3. Etude des Projections Corticales du Nerf Larynge Superieur. Archives Italiennes de Biologie Nov. 1971:109(3):236–52.

Bandler R, Tork I. Midbrain Periaqueductal Grey Region in the Cat has Afferent and Efferrent Connections with Solitary Tract Neuclei. Neuroscience Letters Feb. 10, 1987; 74(1):106.

Barillot JC, Mei N. Modification, Au Niveau du Noyau du Faisceau Solitaire, de l'Excitabilite des Terminaisons de Fibres Vagales ou Laryngees d'origine connue. 1964 Etude Unitaire, pp. 395–396.

Berger A.J. Dorsal Respiratory Group Neurons in the Medulla of Cat: Spinal Projections, Responses to Lung Inflation and Superior Laryngeal Nerve Stimulation. Brain Research Oct. 28, 1977; 35(2):231–54.

Berkley KJ, Schofield SL. Relays from the Spinal Cord and Soitary Nucleus Through the Parabrachial Nucleus to the Forebrain in the Cat. Brain Research Oct. 8, 1990; 529 (1–2):333–8.

Boushey HA, Richardson PS, Widdicombe JG. Reflex Effects of Laryngeal Irritation on the Pattern of Breathing and Total Lung Resistance. Journal of Physiology Jul. 1972;224(2);501–13.

Boushey HA, Richardson PS, Widdicombe JF, Wise JC. The Response of Laryngeal Afferent Fibers to Mechanical and Chemical Stiimuli. Journal of Physiology Jul. 1974;240(1):153–75.

Callanan D, Dixon M, Widdicombe JG, Wise JC. Responses of Geese to Inhalation of Irritant Gases and Injections of Phenyl Diguanide, Respiration Physiology (1974) pp. 157–166.

Car A, Jean A, Roman C. A Pontine Primary Relay for Ascending Projections of the Superior Laryngeal Nerve. Exp. Brain Res. 1975; 22:197–210.

Choudry NB, Fuller RW. Sensitivity of the Cough Reflex in Pateints with Chronic Cough. European Respiratory Journal 5(3):296–300, Mar. 1992.

Chung, K, Ambrogio F, Sant Ambrogio G. The Fiber composition of the Superior Laryngeal Nerve. FASEB Journal 1993; 7:A402.

Daniels SK, Brailey K, Priestly DH, Herrington LR, Weisberg LA, Foundas AL. Aspiration in Patients with Acute Stroke. Arch Phys Med Rehabil vol. 79, Jan. 1998, pp. 14–19.

Das RM, Jeffery PK, Widdicombe JG. The Structure and Function of Intra–Epithelial Nerve Fibers of the REspiratory Tract in the Cat [Proceedings]. Journal of Physiology Aug. 1977;270(1):39P–40P.

Buchholz, DW. Dysphagia Associated with Neurological Disorders [Review] Acta Oto–Rhino–Laryngologica Belgica. 48(2):143–55,1994.

DePippo KL, Holas MA, Reding MJ. Validation of the 3–oz. Water Swallow Test for Aspiration Following Stroke. Arch. Neurol. Feb. 1994, vol. 5, pp. 119–120.

Dyachenko YE, Preobrazhensky NN. Funktsional'naia Differentsiatsiia Afferentov Verkhnegortannogo Nerve Koshki. [Russian: Functional Differentiation of Afferents of Superior Laryngeal Nerve in the Cat]. Neirofiziologiia 1984;16(6):777–83.

Droulias C, Tzinas S, Harlaftis N, Akin JT, Jr. Gray, SW, Skandalakis, JE. The Superior Laryngeal Nerve. American Surgeon Sep. 1976;42(( ):635–8.

Fujimura M, Sakamoto S, Kamio Y, Matsuda T. Cough Receptor Sensitivity and Bronchial Responsiveness in Normal and Asthmatic Subjects. European Respiratory Journal Mar. 1992;5(3):291–5.

Fujimura M, Sakamoto S, Kamio Y, Matsuda T. Effects of Methacholine Induced Bronchoconstriction and Procateral Induced Bronchodilation on Cough Receptor Sensitivity to Inhaled Capsaicin and Tartaric Acid. Thorax Jun. 1992;47(6);441–5.

Fujimura M, Sakamoto S, Kamio Y, Matsuda T. Sex Difference in the Inhaled Tartaric Acid Cough Treshold in Non–Atopic Healthy Subjects. Thorax Aug. 1990;45(8):633–4.

Fukuyama T, Umezaki T, Shin T. Detection of Laryngeal Sensory–Evoked Potentials (LSEPs) in the Cat. Oct. 1993 Amer. Academy of Otolaryngology., pp. 748–752.

Fuller R, Hansson L., Karlsson JA. Neurophysiology of the Cough Reflex [Letter]. European Respiratory Journal. 9(3):622–4, Mar. 1996.

Gerhardt T, Bancalari E. Maturational Changes of Reflex Influencing In Newborns. Amer. Physiological Society 1981. pp. 1282–1285.

Glogowska M., Stransky A., Widdicombe JF. Reflex Control of Discharge in Motor Fibers to the Larynx. Journal of Physiology. 239(2):368–79, Jun. 1974.

Guyton AC. Testbook of Medical Physiology (1991, 8th ed.) pp. 402–413.

Guz A, Noble MIM, Widdicombe JF, Trenchard D. Mushin WW. Peripheral Chemoreceptor Block in Man. Respiration Physiology. 1(1):38–40,1966.

Guz A, Noble MIM, Widdicombe JF, Trenchard D., Mushin WW, Markey AR. The Role of Vagal and Glossopharyngeal Afferent Nerves in Respiratory Sensation, Control of Breathing and Arterial Pressure Regulation in Conscious Man. Clinical Science. 30(1):161–70, Feb. 1966.

Hanacek J, Widdicombe JF. Influence of Lung Stretch Receptors on the Cough Reflex in Rabbits, 1983 Lung Stretch and Coughs, pp. 161–168.

Hardy SG. Medullary Projections to the Vagus Nerve and Posterolateral Hypothalamus. Anatomical Record Jun. 1995; 242(2):251–8.

Hedges JE, Bridges CJ. Stimulation of the Cough Reflex. American Journal of Nursing. 68(2):347–8, Feb. 1968.

Holstege G, Meiners L, Tan K. Projections of the Bed Nucleus of the Stria Terminalis to the Mesencephalon, Pons and Medulla Oblongata in the Cat. Experimental Brain Research 1984;58(2):379–91.

Hopkins DA, Holstege G. Amygdaloid Projections to the Mesencephalon, Pons and Medulla Oblongata in the Cat. Experimental Brain Research Aug. 15, 1978; 32(4):529–47.

Horner J, Braser SR, Massey EW. Aspiration in Bilateral Stroke Patients: A Validation Study. Neurology. 43(2):43–3, Feb. 1993.

Horner J, Buoyer FG, Alberts MJ, Helms MJ. Dysphagia Following Brain–Stem Stroke: Clinical Correlates and Outcome. Archives of Neurology Nov. 1991; 48(11):1170–3.

Horner J, Massey EW. Silent Aspiration Following Stroke. Neurology. 38(2):317–9, Feb. 1988.

Horner J, Massey EW, Brazer SR. Aspiration in Bilateral Stroke Patients. Neurology, 40(11):1686–8, Nov. 1990.

Horner J, Massey EW, Riski JE, Lathrop DL, Chase KN. Aspiration Following Stroke: Clinical Correlates and Outcome. Neurology. 38(9):1359–62, Sep. 1988.

Iscoe S, Feldman JL, Cohen MI. Properties of Inspratory Termination by Superior Laryngeal and Vagal Stimulation. Respiration Physiology. 35(3):353–66, Apr. 1979.

Javorka K, Tomori Z, Zavarska L. 1985 Upper Airway Reflexes in Newborns with Respiratory Distress Syndrome. pp. 345–349.

Javorka K, Tomori Z, Zavarska L. 1980 Protective and Devensive Airway Reflexes in Premature Infants. Physiologia Bohemoslovaca pp. 29–35.

Jean A. Brainstem Control of Swallowing: Localization and Organization of the Central Pattern Generator for Swalling. 1990 Neurophysiology of the Jaws and Teeth. pp. 294–321.

Jean A, Car A, Roman C. Comparison of Activity in Pontine Versus Medullary Neurones During Swallowing. Experimental Brain Research. 22(2):211–20, 1975.

Jordan D, Donoghue S, Spyer KM. Respiratory Modulation of Afferent Terminal Excitability in the Nucleus Tractus Solitarius. Journal of the Autonomic Nervous System. 3(2–4:2991–7, Apr. 1991.

Jeffery PK, Korpas J, Widdicombe JF. Intraepithelial Nerve Fibers of the Cat Larynx and the Expiration Reflex [proceedings]. Journal of Physiology. 275:35P–36P, Feb. 1978.

Kamei J, Hosokawa T, Yanaura S, Hukuhara T. Involvement of Central Serotonergic Mechanisms in the Cough Reflex. Japanese Journal of Pharmacology. 42(4):531–8, Dec. 1986.

Kamei J, Hukuhara T, Kasuya Y. Dopaminergic Control of the Cough Reflex as Demonstrated by the Effects of Apomorphine. European Journal of Pharmacology. 141(3):511–3, Sep. 23, 1987.

Karlsson JA. Airway Anaesthesia and the Cough Reflex. [Review] Bulletin European de Physiopathologie Respiratoire. 23 Suppl 10:29s–36s, 1987.

Karlsson JA, Hanson L, Wollmer P, Kahlback M. Regional Sensitivity of the Respiratory Tract to Stimuli Causing Cough and Reflex Bronchoconstriction. Respiratory Medicine Jan. 1991;85 (Supplement A) 47–50.

Karlsson JA, Sant Ambrogio G, Widdicombe J. Afferent Neural Pathways in Cough and Reflex Bronchoconstriction. Journal of Applied Physiology Sep. 1988;65(3):1007–23.

Katsumata U, Sekizawa K, Ebihara T, Susaki H. Aging Effects on Cough Reflex [letter]. Chest. 107(1):290–1, Jan. 1995.

Kearney HL. Unusual Cases of Cicatricial Stricture of the Esophagus. 1934 OTOL. pp. 527–531.

Kessler JP, Jean A. Inhibition of the Swallowing Reflex by Local Applicaiton of Serotonergic Agents into the Nucleus of the Solitary Tract. European Journal of Pharmacology. 118(1–2:77–84), Nov. 26, 1985.

Kim YH, Hong WO, Kim KM, Kim HY. 1997 Superior Laryngeal Nerve Brain Stem Evoked Response in the Cat. Ann. Otol. Thinol. Laryngol. 106:101–8.

Korpas J. Recent Advances Concerning the Cough Reflex (Chairman's Introduction). [Review] Acta Physiologica Hungarica. 70(2–3:161–5, 1987.

Korpas J, Widdicombe JG. Aspects of the Cough Reflex [Review] Respiratory Medicine. 85 Suppl A:3–5, Jan. 1991.

Lalakea ML, Anonsen CK, Hannley M. Laryngeal Brainstem Evoked Response: A Developmental Study. Laryngoscope 100: Mar. 1990, pp. 294–301.

LeFrock JL, Clark TS, Davies B, Klainer AS. Aspiration Pneumonia. A Ten–Year–Review. The American Surgeon May 1979.

Lemere F. Innervation of the Larynx. I. Innervation of Laryngeal Muscles. The American Journal of Anatomy, vol. 51, No. 2, pp. 417–437, 1932.

Lemere F. Innervation of the Larynx. II> Ramus Anastomoticus and Ganglion Cells of the Superior Laryngeal Nerve. American Journal of anatomy 1932; 54:389–407.

Lewis DJ, Prentice DE. The Ultrastructure of a Rat Laryngeal Epithelia. Journal of Anatomy 1980; 130:617–32.

Lowey AD, Burton H. Nuclei of the Solitary Tract: Efferent Projections to the Lower Brain Stem and Spinal Cord of the Cat. Journal of Comparative Neurology Sep. 15, 1978:181(2):421–49.

Lucier GE, Egizil R., Dostrovsky JO. 1986 Projections of the Internal Branch of the Superior Laryngeal Nerve of the Cat. Brain Res. Bull. 15:713–21.

Manchanda AK, Aneia IS. Afferent Projections of Superior Laryngeal Nerve in the Medulla Oblongata—Localization of the 'Swallowing Centre'. Indian Journal of Physiology & Pharmacology. 16(1):67–73, Jan. 1972.

Mantyh PW, Hunt SO. Neuropeptides are Present in Projection Neurones at All Levels in Visceral and Taste Pathways: from Periphery to Sensory cortex. Brain Research. 99(2):297–312, May 14, 1984.

Mathew OP, san tAmbrogio G, Fisher JT, Sant Ambrogio FB. Respiratory Afferent Activity in the Superior Laryngeal Nerves. Respiration Physiology (1984 58, 41–50.

Matsumoto S. The Activities of Lung Stretch and Irritant Receptors During Cough. Neuroscience Letters, 90 (1988) 125–129.

McRitchie DA, Tork I. The Internal Organization of the Human Solitary Nucleus. Brain Research Bulletin 1993;31(1–2):171–93.

Mei NN, Condamin M, Rousseau A. Composition Histologique du Nerf Larynge Superieur du Chat. [Histological Composition of the Superior Laryngeal Nerve of the Cat]. Comptes Rendus des Seances de la Societe de Biologie et de Ses Filiales Jul. 1968; 162(1):145–9.

Mei NN, Nourigat B. Etude Electrophysiologique des Neurones Sensitifs du Nerf Laryne Superieur. [Electrophysiologic Study of the Sensory Neurons of the Superior Laryngeal Nerve]. comptes Rendus des Seances de la Societe de Biologie et de Ses Filliales Jul. 1968; 162(1):149–53.

Miller AD, Bianchi AL, Bishol BO (eds). 1997 Neural Control of the Respiratory Mulcles. Boca Raton CRC Press.

Miller AJ, Loizzi RF. Anatomical and Functional Differentiation of Superior Larynegeal Nerve Fibers Affecting Swallowing and Respiration. Experimetal Neurology Feb. 1974;42(2):369–87.

Montalt J, Basterra J, Armengot M, Barona R. Superior Laryngeal Nerve Evoked Potentials: An Experimental Study in the Rabbit. Laryngoscope 104:May 1994, pp. 627–630.

Morice AH, Higgins KS, Yeo WW. Adaptation of Cough Reflex with Different Types of Stimulation. European Respiratory Journal. 5(7):841–7, Jul. 1992.

Neafsey EJ, Hurley–Guis KM, Aranitis D. The Topographical Organization of Neurons in the Rat Medial Frontal, Insular and Olfactory Cortex Projecting to the Solitary Nucleus Olfactory Bulb, Periaqueductal Gray and Superior Colliculus. Brain Research. 377(2):561–70, Jul. 9, 1986.

Nishino T, Tagaito Y, Isono S. Cough and Other Reflexes on Irritation of Airway Mucosa in Man. Pulmonary Pharmacology (1996) 9, 285–292.

Nosaka, S. Solitary Nucleus Neurons Transmitting Vagal Visceral Input to the Forebrain Via a Direct Pathway in Rats. Expieirmental Neurology Sep. 1984;84(3):493–505.

O'Connell F, Thomas VE, Pride NB. Adaptation of Cough Reflex with Different types of Stimulation [letter comment]. Euroean Respiratory Journal. 5(10):1296–7, Nov. 1992.

"FDA Request for Designation", printed Apr. 8, 1998; Sponsor: Dysphagia Systems, Inc. pp. 1–9.

"Pneumoflex Neuroscientific Description", FDA Neuroscientific Master; printed Apr. 7, 1998; pp. 1–6.

Pneumoflex—Research Studies on the Safety and Nature of L–Tartaric Acid; FDA—Safety and Scientific Studies; Dysphagia Systems, Inc., pp. 1–22.

Addington WR, Stephens RE, Gilliland K and Miller SP."Tartaric Acid–Induced Cough and the Laryngeal Evoked Potential", pp. 1–14. (in press).

Addington, WR, Stephens, RE and Goulding RE. anesthesia of the Superior Laryngeal Nerve and Tartaric Acid–Induced Cough. pp. 1–15. (in press).

Stephens RE, Wendel KH and Addington, WR. "The Laryngeal Evoked Potential (LEP) and Laryngeal Cough Reflex", 28 pages. (in press).

Addington WR, Stephens Re, Gillilnd K and Rodriguez M. "Assessing the Laryngeal Cough Reflex and the Risk of Developing Pneumonia After Stroke." pp. 1–22. (in press).

Pack R.J.., Al–Ugaily L.H., Widdicombe, J.G.—The innervation of the trachea and extrapulmonary bronchi of the mouse. Cell & Tissue Research. 238(1):61–8, 1984.

Paintal A.S.,—Vagal Sensory Receptors and their Reflex Effects. Physiological Review 1973; 53(1): 159–225 Jan..

Palmer J.B., Duchane A.S.—1991. Rehabilitation of Swallowing Disorders Due to Stroke. Physical Medicine and Rehabilitation Clinics of North America 1991 2(3) 529–546.

Pantaleo T, Corda M.—Expiration–related Neurons in the Region of the Retrofacial Nucleus: Vagal and Laryngeal Inhibitory Influences. Brain Research Dec. 16, 1985; 359(1–2): 343–6.

Pimpaneau A. O'Brien J., Albe–Fessard D.—Afferences du Nerf Larynge Superieur et du Nerf Vague Vers les Aires Corticales de Projections et de Commande de la face, de la Langue et du Larynx Chez le Singe. Journal de Physiologe 1967; 59 (4 Suppl): 474.

Sant' Ambrogio g.—Afferent Pathways for Cough Reflex. [Review] Bulletin European de Physiopathologie Respiratorie 1987; 23 (Suppl 10): 19s–23s.

Sant'Ambrogio g.—1996. Role of the Larynx in Cough.

Sant' Ambrogio G., Mathew O.P., Sant' Ambrogio F.B.—Role of Intrinsic Muslces and Tracheal Motion in Modulating Laryngeal Receptors. Respiration Physiology. 61(3): 289–300, Sep. 1985.

Sant' Ambrogio G., Sant' Ambrogio, F. B., Davies A.—Airway Receptors in Cough. Bulletin Eurpean de Physiopathologie Respiratoire Jan.–Feb. 1984; 20(1): 43–7.

Sant' Ambrogio G., Sant' Ambrogio F. B.,—(1996) Role of Laryngeal Afferents in Cough.

Sant' ambrogio G.G., Tsubone H., Sant' ambrogio F. B.—Sensory Information from the Upper Airway: Role in the Control of Breathing. [Review] Respiration Physiology Oct. 1995; 102(1): 1–16.

Sasaki, C. T., Newman A., Akitaya T., Kirchner J.A.—Effect of Microaerosol Inhalation on the Pattern of Breathing. Annals of Otology, Rhinology & Laryngology. May–Jun. 1975 (84(3 pt 1): 344–9.

Sato I., Shimada K. 1995 Arborization of the Inferior Laryngeal Nerve and Internal Nerve on the Posterior Surface of the Larynx. Clin. Anat. 8:379–387.

Schugt H. P. the Piriform Sinus: Anatomic and Clinical Observations with a Review of the Literature. Arch. Otol. 1940; 31: 626–44.

Sekizawa K., Ujiie Y., Nakazawa H., Sasaki H., Katsumata U., Takasugi R. Abnormalities in Cough Reflex. (abstract), Japanese Journal of Geriatrics, v28, pp. 308–310, 1991.

Sellick H., Widdicombe, J.G. Vagal Deflation and Inflation Reflexes Mediated by Lung Irritant Receptors, Quarterly Journal of Experimental Physiology, pp. 153–163, v55, 1970.

Sessle, G. J., Ball, G.J., Lucier, G. E., Suppressive Influences from Periaqueductal Gray and Nucleus Raphe Mangus on Respiration and Related Reflex Activities and on Solitary Tract Neurons, and Effect of Naloxone. Brain Research— 216 (1981) 145–161.

Shannon, R., Bolser, D. C., Lindsey, G. G. 1997 Neural Control of Coughing and Sneezing. In Neural Control of the Respiratory Muscles. A. D. Miller, A. L. Bianchi, and B. P. Bishop (eds.). Boca Raton: CRC Press, pp. 216–19.

Simonsson, G. B., Jacobs, F. M., Nadel, J.A. Role of Autonomic Nervous System and the Cough Reflex in the Increased Responsiveness of Airways in Patients with Obstructive Airway Disease. Journal of Clinical Investigation. 46(11): 1812–8, Nov. 1967.

Stockwell, M., Lang, S., Yip, R., Zintel, T., White, C., Gallagher, C. G. Lack of Importance of the Superior Laryngeal Nerves in Citric Acid Cough in Humans. Journal of Applied Physiology. 75(2): 613–7, Aug. 1993.

Stockwell, M., Lazanoff, S., Lang, S., Nyssen, J. Superior Laryngeal Nerve Block: An Anatomical Study. 1995 Clinical Anatomy 8:89–95.

Stransky, A., Szereda–Przestaszewska, M., Widdicombe, J.G. The Effects of Lung Reflexes on Laryngeal Resistance and Montoneurone Discharge. J. Physiol (1973) pp. 417–438.

Suzuki, M., Sasaki, C.T. Effect of Various Sensory Stimuli on Reflex Laryngeal Adduction. Annals of Otology, Rhinology & Laryngology Jan.–Feb. 1997; 86(1 pt 1): 30–6.

Suzuki, M., Sasaki, C. T. Initiation of Reflex Glottic Closure. Annals of Otology, Rhinology & Laryngology May– Jun. 1976; 85 (3 pt 1): 382–6.

Suzuki, M., Kirchner, J. A. Sensory Fibers in the Recurrent Laryngeal Nerve: An Electrophysiological Study of some Laryngeal Afferent Fibes in the Recurrent Laryngeal Nerve of the Cat, Annals of Otology, Rhinology, and Laryngology, v78, pp. 21–31, 1969.

Szereda–Przestaszewska, M., Widdicombe, J.G. Reflex Changes in the Lumen of the Cat Larynx Due to Chemical Irritation of the Upper Airways. Journal of Physiology—Jul. 1973; 232(2): 80p–81p.

Takagi S., Umezaki, T., Shin, T. Convergence of Laryngeal Afferents with Different Natures Upon Cat NTS Neurons. Brain Research Bulletin—vol. 38. No. 3, pp. 261–268, 1995.

Takahama K., Miyata, T. [Cough—Diversity and the Peripheral Mechanisms of Production]. Nippon Yakurigaku Zasshi—Folia Pharmacologica Japonica Feb. 1995; 105(2): 41–52.

Tatar, M., Sant' Ambrogio, G., Sant' Ambrogio, F. B. Laryngeal and Tracheobronichial Cough in Anesthetized Dogs, Journal of Applied Physiology, v76, pp. 2672–2679, 1994.

Tell, F., Fagni, L., Jean, A. Neurons of the Nucleus Tractus Solitarius, in vitro, Generate Bursting Activities by Solitary Tract Stimulation. Exp. Brain Res. (1990) 79: 436–440.

Terreberry, R. R., Neafsey, E/J. Rat Medial Frontal Cortex: A Visceral Motor Region with a Direct Projection to the Solitary Nucleus. Brain Research Nov. 14, 1983; 278 (1–2): 245–9.

Terreberry, R.R., Neafsey, E.J. The Rat Medial Frontal Cortex Projects Directly to Autonomic Regions of the Brainstem. Brain Research Bulletin Dec. 1987; 19 (6): 639–49.

Traxel, R.M., Prudlow, W. F., Kampine, J.P., Coon, R.L., Zuperku, E.J. Annals of Otology, Rhinology & Laryngology. 85(5 pt 1): 664–9, Sep.–Oct. 1976.

Twitchell, T.E. The Restoration of Motor Function Following Hemiplegia in Man. Brain 1951; 74: 443–80.

van de Kooy, D., Koda, L.Y., McGinty, J.F., Gerfen, C.R., Bloom, F.E. The Organization of Projections from the Cortex, Amygdala, and Hypothalamus to the Nucleus of the solitary Tract in Rat. Journal of Comparative Neurology Mar. 20, 1984: 224(1): 1–24.

van de Kooy, D., McGinty, J.F., Koda, L.Y., Gerfen, C.R., Bloom, F.E. Visceral Cortex: A Direct Connection from Prefrontal Cortex to the Solitary Nucleus in Rat. Neuroscience Letters 1982: 33(2): 123–7.

Vogel, P.H.—The Innervation of the Larynx of Man and the Dog. II. Ramus Anastomoticus and Ganglion Cells of the Superior Laryngeal Nerve. American Journal of Anatomy 1952; 90: 427–47.

Weerasuriva, A., Bieger, D., Hockman, C.H.—Basal Forebrain Facilitation of Reflex Swallowing in the Cat. 1979 Brain Res 174: 119–133.

Widdicombe, J.G.—Sensory Neurophysiology of the Cough Reflex. 1996 J Allergy Clin Immunol 98 (5 part 2): s84–s90.

Widdicombe, J.G.—Neurophysiology of the Cough Reflex 1995 Eur Respir J 8:1193–1202.

Widdicombe, J.G.—Mechanism of Cough and its Regulation [Review] European Journal of Respiratory Diseases—Supplement 110:11–20, 1980.

Widdecombe, J.G.—Nasal and Pharnygeal Reflexes: Protective and Respiratory Functions. In Respiratory Function of the Upper Airway. G. Sant' Ambrogio and O.P. Mathew, Eds. Marcel Drekker, NY. 1988; pp. 233–58.

Widdicombe, J.G.—Reflexes from the Lungs and the Respiratory Tract. 1971 Acta Physiologica Polonica 22 (3 suppl 2): 397–418.

Widdicombe, J.G.—Sensory Innervation of the Lungs and Airways. Progress in Brain Research 1986; 67:49–64.

Widdicombe, J.G.—Studies on Afferent Airway Innervation. American Review of Respiratory Disease 1977: 115(6 pt 2): 99–105.

Widdicombe, J.G.—Modes of Excitation of Respiratory Tract Receptors. Progress in Brain Research 1976; 43:243–52.

Widdicombe, J.G.—Pulmonary and Respiratory Tract Receptors 1982 J Exp Biol 100:41–57.

Widdicombe, J.G.—Mediators of Reflexes and Bronchoconstriction [Review] European Journal of Respiratory Disease—Supplement. 129:65–94, 1983.

Widdicomber, J.G.—Chemoreceptor Control of Airways 1992—Respiration Physiology 87:373–81.

Widdicomber, J.G.—Lungs and Inspiratory Tract Afferences. Introductory Talk. pp. 233–40. In: Duron B., ed *Respiratory Centers and Afferent Systems*. Paris, INSERM, 1976.

Widdicombe, J.G. [Laryngeal Receptors in the Expiratory Reflex] 1986 Bratislavskie Lekarskie Listy 85(4): 424–9.

Widdicombe, J.G.—Proceedings: Reflex Control of Larynx. Bulletin de Physio–Pathologie Respiratorie 11(2): 102P–103P, Mar.–Apr. 1975.

Widdicombe, J.G.—Pathophysiology of Lung Reflexes. Bulletin de Physio–Pathologie Respiratorie. 10(1):65–9, Jan.–Feb. 1974.

Widdicombe, J.G.—Lung Reflexes. Bulletin de Physio–Pathologie Respiratorie. 8(3): 723–5, May–Jun. 1972.

Widdicombe, J.G.—Reflex Function of the Lung: Round Table Discussion . Bulletin de Physio–Pathologie Respiratorie. 10(1): 85–7, Jan.–Feb. 1974.

Widdicombe, J.G. Glogowska, M.,—Relative Roles of Irritant, Type—J and Pulmonary Stretch Receptors in Lung Reflexes 1973 Acta Neurobiol Exp 33:21–31.

Widdicombe, J.G., Sant' Ambrogio, G., Mathew, O.P.—Nerve Receptors of the Upper Airway, In Respiratory Function of the Upper Airway. G. Sant' Ambrogio and O.P. Mathew, Eds, Marcel Drekker, NY 1988; pp. 193–231.

Widdicombe, J.G., Sterling, G.M.,—The Autonomic Nervous System and Brething [Review] 1970 Archives of Internal Medicine 126:311–29.

Widdicombe, J.G., Tartar, M.—Upper Airway Reflex Control. Annals of the New York Academy of Sciences 1988; 533:252–61.

Yamamoto, Y., Hosono, I., Atoji, Y., Suzuki, Y.—Morphological Study of the Vagal Afferent Nerve Endings in the Laryngeal Mucosa of the Dog 1997 Anatomischer Anzeiger 179:65–73.

Yanaura, S., Hosokawa, T., Kitagawa, H., Yamatake, Y.,—Influence of Tracheal Muscular Tone on the Initiation of Cough Reflex 1978 Japan J. Pharmacol 28(3): 447–455.

Yanaura, S., Kamei, J., Goto, K., Hosokawa, T., Hiramori, T., Misawa, M., Hukuhara, T.,—A Quantitative Analysis of the Phrenic Nerve Activities During the Cough Reflex 1982 Folia Pharmacol Japan 79: 543–550.

Yanaura, S., Iwase, H., Sato, S., Nishimura, T.—A New Method for Induction of the Cough Reflex 1974 Japan J. Pharmacol 24(3): 453–460.

Yanaura S., Nishimura, T., Sasao, T., Sone, Y.—Proceedings: Pharmacological Studies of the Respiratory Tract. 9. A Study of Cough–Like Reflex. 1974 Japanese Journal of Pharmacology. 24:s29.

Yanaura, S., Nishimura, T. Hosokawa, T., Abe, Y., Iwase, H.—Pharmacological Studies on the Cough–Like Reflex Induced by Chemical Stimulation. [Japanese] Nippon Yakurigaku Zasshi—Folia Pharmacologica Japonica. 74(3): 345–52, Apr. 1978.

Yanaura, S. Hosokawa, T., Kitagawa, H., Kamei, J., Misawa, M.—Effects of Peripheral Airway Response on the Cough Reflex. [Japanese] Nippon Yakurigaku Zasshi—Folia Pharmacologica Japonica. 76(8):709–16,Nov. 1980.

Yunaura, S., Hosokawa, T., Kitagawa, H., Misawa, M.—Reflex Effects of Cough Reflex on the Tracheobronichial Vascular Tone. [Japanese] Nippon Yakurigaku Zasshi—Folia Pharmacologica Japonica. 78(1): 9–16, Jul. 1981.

Yin, S.S., Qiu, W.W., Stucker, F.J., Hoasjoe, D.K., Aarstad, R.F., Batchelor, B.M.—1997 Laryngeal Evoked Brainstem Responses in Humans: A Prelininary Study. Laryngoscope 107:1261–6. Sep. 1997.

Yoshida, Y., Tonaka, Y., lMitsumasu, T., Hirano, M., Kanaseki, T.,—1986 Peripheral Course and Intramucosal Distribution of the Laryngeal Sensory Nerve Fibers of Cats. Brain Research Bulletin 17: 95–105.

Zelenak, J.P., Alarie, IY., Weyel, D.A.—Assessment of the Cough Reflex Caused by Inhalation of Sodium Lauryl Sulfate and Citric Acid Aerosols. Fundamental & Applied Toxicology. 2(4): 177–80, Jul.–Aug. 1982.

Rogers, R.C., Nelson, D.O.—Neurons of the Vagal Division of the Solitary Nucleus Activated by the Paraventricular Nucleus of the Hypothalamus. Journal of the Autonomic Nervous System Apr. 1984; 10(2): 193–7.

Sekizawa, K., Yjiie, Y., Itabashi, S., Sasaki, H., Takishima, T.—Lack of Cough Reflex in Aspiration Pneumonia. [Letter] Lancet May 19, 1990;335 (8699):1228–9.

Griffin et al., "Aspiration pneumonia and the laryngeal mask airway," Anaesthesia, pp. 1039–1040, Dec. 1990.

Kingston et al., "Increased incidence of nosocomial pneumonia in mechanically ventilated patients with subclinical aspiration," American Journal of Surgery, pp. 589–592, May 1991.

Handerhan, "Guarding against aspiration pneumonia," Nursing, pp. 96–97, Oct. 1992.

Morice, "Inhalation cough challenge in the investigation of the cough reflex and antitussives," Pulmonary Pharmacology, pp. 281–284, Oct. 1996.

ASPIRATION SCREENING PROCESS FOR ASSESSING POST SURGERY PATIENT'S RISK FOR PNEUMONIA

FIELD OF THE INVENTION

The present invention relates in general to the field of post surgery patient recovery, and is particularly directed to an involuntary cough-based process for determining whether a patient, who has undergone general anesthesia, is at risk for developing aspiration-based pneumonia. This is accomplished by causing the patient to inhale an aerosol chemostimulant that will stimulate a fully functional (recovered) sensory innervation of the patient's larynx, causing the patient to involuntarily cough. If the patient fails to cough, however, it is inferred that the patient's involuntary cough reflex is not yet fully functional, and that the patient is at risk of developing aspiration-based pneumonia.

BACKGROUND OF THE INVENTION

Any patient who is to be given a general anesthetic for a surgical procedure is intubated prior to surgery. The anesthetic effectively pharmacologically suppresses brainstem function, inluding a variety of involuntary physiological responses, not the least of which is the ability to cough and clear the upper airway. These brainstem reflexes are suppressed until the anesthetic wears off. Because the tubing that has been inserted into the patient's airway tends to act like a wick—drawing fluid (e.g., secreted saliva) that may be present in the patient's mouth into the patient's airway and lungs—it is critical that the patient's involuntary cough reflex be fully functional at the time the patient is extubated.

Unfortunately, there is currently no mechanism for accurately determining whether or not the patient's ability to involuntarily clear the airway has been fully restored. Instead, because each patient's anesthesia recovery time is different, the standard medical practice is to have a skilled medical practitioner (e.g., anesthesiologist) observe the patient, and then make an 'educated guess' that the patient's anesthetic state has completely subsided, and that it is 'reasonably safe' to extubate the patient, and allow the patient to receive fluids and/or nutrients by mouth. If the patient's involuntary cough reflex is not yet fully restored, however, the patient is at considerable risk of developing pneumonia, as a result of entry into the airway from the patient's mouth of what would otherwise be expelled secretion and/or foreign matter that could be a substrate for breeding bacteria.

In addition, even in those cases where a patient has the ability to cough both involuntarily and voluntarily, the condition of the patient (for example in the case of coronary bypass surgery) may be such that it is extremely difficult and/or painful to have the patient cough voluntarily to clear and expel secretions, mucous and the like from the patient's airway.

SUMMARY OF THE INVENTION

In accordance with a first embodiment of the present invention, the potential problem of post surgery aspiration-based pneumonia, discussed above, is readily determined by means of an aerosol-based screening process, that determines the ability of an extubated post-op recovery patient, whose involuntary cough reflex in the larynx have been previously anesthetized (as by the application of a general anesthetic) or compromised by intubation, to cough involuntarily and thereby clear the patient's airway of secretion and/or foreign matter that could be a substrate for breeding bacteria and cause pneumonia.

For this purpose, the laryngeal cough reflex of the patient is evaluated by introducing (spray-injecting) an aerosol chemostimulant into the patient's mouth, for the purpose of stimulating irritant similar types of receptors in the patient's larynx. The aerosol inhalant preferably comprises that described in U.S. Pat. No. 5,678,563, entitled: "Aspiration Screening Process for Assessing Need for Modified Barium Swallow Study," the disclosure of which is herein incorporated, comprising a nebulized or aerosol solution of tartaric acid (tartrate) mixed with saline and is delivered by a standard aerosol nebulizer.

Although other receptor specific chemostimulants may be employed, studies involving the inhalation of a tartaric acid reveal that inhalation of twenty percent nebulized tartaric acid will stimulate an involuntary and abrupt 'explosive' cough, one hundred percent of the time in those patients whose laryngeal cough reflexes have fully recovered from the anesthetic and are fully functional. Further, tartaric acid is considered to be safe, does not cause pain or discomfort, and has not been shown to cause bronchoconstriction or complications in asthmatics or smokers when inhaled in an aerosol form.

The tartrate-containing aerosol stimulant may be injected into the patient's mouth by a respiratory therapist, using a nebulizer for a relatively brief period of time. The patient may be tested a plurality times at respectively different stimulant strengths to determine whether and at what aerosol strength an involuntary cough can be elicited. During each successive stimulant application, the patient receives progressively increasing concentrations of the aerosol for a prescribed period of time by tidal breathing at one minute intervals using successively increasing percentage concentrations.

If the patient involuntarily coughs as a result of the introduction of any concentration of aerosol stimulant, the inhalation cough test is terminated, regardless of the percentage of concentrations used. The patient's response to the inhalation test is then graded, for example, as a low pneumonia risk (if the patient coughs immediately in response to the initial aerosol spray and the cough appears strong or normal), or as a high pneumonia risk (where the cough appears weak or the patient does not readily cough in response to the initial concentration spray, but requires a more concentrated aerosol application). If the patient fails to cough for any strength of inhaled aerosol stimulant, the inhalation cough test is terminated, and it is determined that anesthetization of the patient's laryngeal cough reflex has not fully subsided, so that the patient remains at high pneumonia risk and may not be given fluids or nutrients by mouth.

In a second embodiment of the invention, using a procedure termed a "pulmonary toilet," involving repeated applications of the tartaric acid aerosol spray described above, the patient is involuntarily forced to cough multiple times and thereby remove potentially threatening fluid and other matter from the patient's airway. This second embodiment of the invention is employed where the condition of the patient is such that it is extremely difficult and/or painful to have the patient cough voluntarily to clear and expel secretions, mucous and the like from the patient's layrnx.

DETAILED DESCRIPTION

Figure 1:
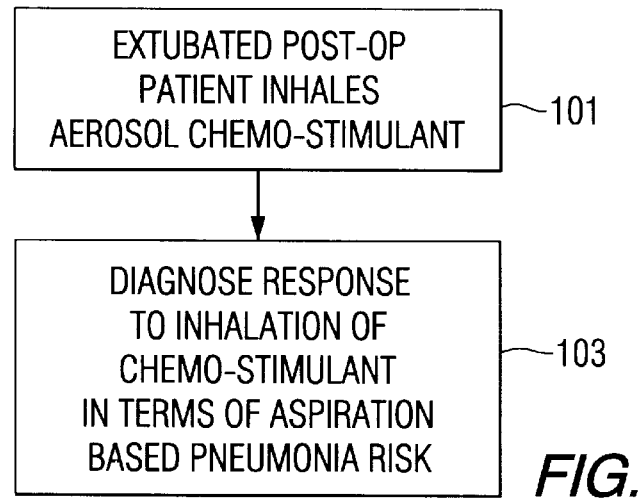
FIG. 1 is a flow diagram of the cough-based screening process for diagnosing whether an extubated post surgery patient is at risk for developing aspiration-based pneumonia in accordance with the present invention.

FIG. 1 is a flow diagram of the steps of the aerosol-based involuntary cough screening process of the present invention for clinically diagnosing whether there is a potential risk for post surgery aspiration-based pneumonia, by introducing (spray-injecting) an aerosol chemostimulant into an extubated patient's mouth, in order to stimulate irritant or similar types receptors in the patient's larynx. During the first step 101, an aerosol chemostimulant is injected into the patient's mouth by a respiratory therapist, using an aerosol inhaler, such as a commercially available Bennett Twin nebulizer, shown at 22 in FIG. 2.

Figure 2:
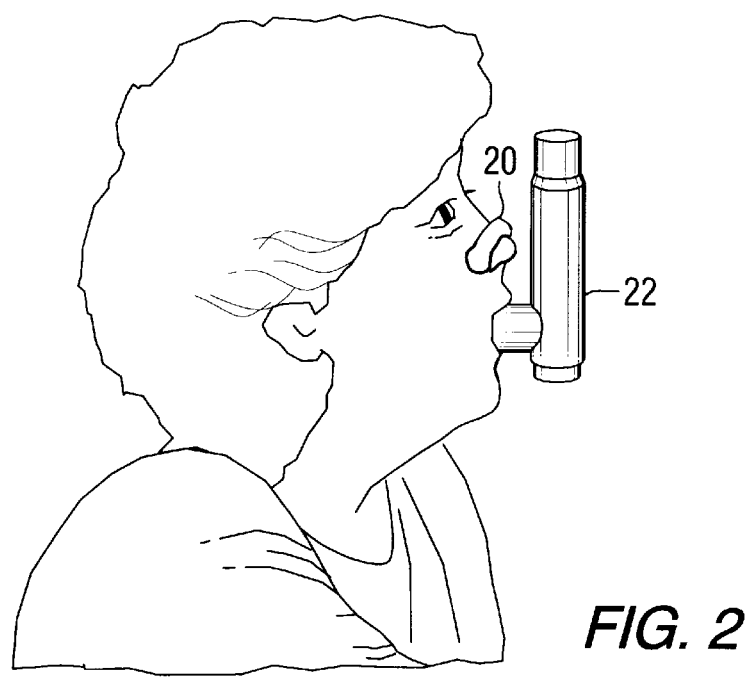
FIG. 2 diagrammatically illustrates the use of an aerosol inhaler in the involuntary cough process of the present invention.

As described briefly above, the aerosol chemostimulant preferably comprises a nebulzed solution of twenty-perecent tartaric acid mixed with saline, as described in the above-referenced patent. Although other receptor specific chemo-stimulants may be employed, studies involving inhaling tartrate, and referenced in the above-identified patent, have shown that tartrate will stimulate an involuntary cough one-hundred percent of the time in normal individuals (i.e. whose laryngeal cough reflexes are functioning normally (not anesthetized)). Moreover, tartrate is considered safe, does not cause pain or discomfort, and has not been shown to cause bronchoconstriction or complications in asthmatics or smokers when inhaled in an aerosol form. During the inhalation cough test, the patient wears a nose-clip 20, as shown in FIG. 2.

The aerosol chemostimulant is preferably inhaled for a prescribed period of time (e.g., on the order of 15 seconds). The nebulizer output spray rate may be on the order of 0.2 ml/min. as a non-limiting example. The patient may be given a plurality of spray applications, up to some prescribed maximum (e.g., three times) at different stimulant strengths, in an effort to elicit a cough. During these successive chemostimulant applications, the patient receives progressively increased concentrations of the aerosol for the prescribed period of time by tidal breathing at one minute intervals using successively increasing percentage concentrations (e.g. 20, 50 and 80 percent).

If, for any aerosol application, the patient involuntarily coughs, the inhalation cough test is terminated, regardless of the percentage of concentrations used. If no involuntary cough is elicited after the maximum number of spray applications and maximum concentration, the test is also terminated. The patient's response to the inhalation test is then graded in STEP 103 as either a low pneumonia risk (as in the case where the patient coughs immediately in response to the initial aerosol spray), or a high pneumonia risk (as in the case where a cough is present but decreased, does not readily cough in response to the initial concentration spray, but requires a more concentrated aerosol application, or does not cough at all).

As pointed out above, should the patient fail to involuntarily cough, irrespective of the strength of inhaled aerosol stimulant, it is determined that anesthetization of the patient's laryngeal cough reflex has not fully subsided, and the patient is diagnosed as remaining at high risk for aspiration-based pneumonia due to a neurologically unprotected airway. This warrants consideration re-intubation, putting the patient on a restricted diet, NPO, or alternative feeding strategies, such as percutaneous endoscopic gastrostomy, until the patient's involuntary cough reflex has completely recovered.

Figure 3:
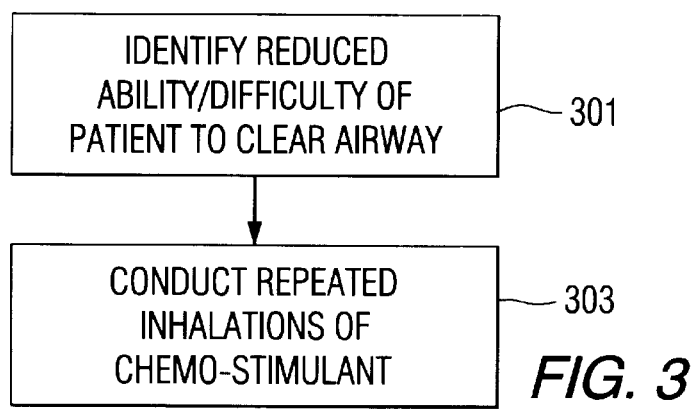
FIG. 3 is a flow diagram of the cough-based therapy process for forcing a patient to clear the patient's airway through repeated applications of a cough reflex stimulating aerosol.

In accordance with a second 'treatment' embodiment of the invention, a flow diagram of which is shown in FIG. 3, the inability of a patient to expel potentially threatening fluid and matter from the patient's airway, identified at step 301, is overcome by repeated applications, as shown by step 303, of an aerosol chemostimulant spray, as described above in the first embodiment. In the second embodiment, the concentration employed is preferably the lowest concentration which is effective to stimulate a cough. As described above, such an inability of the patient to clear and expel secretions, mucous and the like from the patient's larynx may occur in those instances where the condition of the patient is such that it is extremely difficult and/or painful to have the patient cough voluntarily.

The number of aerosol chemostimulant repetitions will depend upon the secretion-expelling response of the patient to each application. After each application, and associated expelling of secretions by the patient, the patient is examined to determine whether an additional application aerosol chemostimulant is required, to clear the airway for that treatment. The patient is continuously monitored and the procedure is repeated at whatever intervals are necessary to maintain the patient's airway free of fluid and secretions that constitute a risk of aspiration-based pneumonia.

As will be appreciated from the foregoing description, whether an extubated post surgery patient is at risk for aspiration-based pneumonia is readily determined in accordance with the present invention, by requiring the patient to inhale an aerosol that will stimulate a fully functional sensory innervation of the patient's larynx, and cause the patient to cough involuntarily. Depending upon the patient's cough response or lack thereof, the patient can be graded to determine whether the patient is at risk for pneumonia. In addition, the inability of a patient to readily expel potentially threatening fluid and matter from the patient's airway can be remedied by repeated applications of the aerosol chemostimulant spray of the first embodiment.

While we have shown and described several embodiments in accordance with the present invention, it is to be understood that the same is not limited thereto but is susceptible to numerous changes and modifications as known to a person skilled in the art, and we therefore do not wish to be limited to the details shown and described herein but intend to cover all such changes and modifications as are obvious to one of ordinary skill in the art.

What is claimed is:

1. A method of evaluating a patient, who has been anesthetized in the course of a surgical procedure, to determine whether the patient is at risk to a develop aspiration-based pneumonia as a result of the incomplete functional recovery of the patient's involuntary cough reflex, comprising the steps of:

(a) causing the patient, subsequent to the surgical procedure, to inhale an aerosol that is effective to stimulate a sensory innervation of a normally functional patient's larynx, causing the patient to cough;

(b) in response to the patient failing to cough as a result of inhaling said aerosol in step (a), diagnosing said patient at risk for aspiration-based pneumonia, but in response to said patient coughing as a result of inhaling said aerosol in step (a), diagnosing said patient as being free of risk for aspiration-based pneumonia.

2. A method according to claim 1, wherein step (a) comprises causing said patient to inhale an aerosol containing a chemical that is effective to stimulate irritant or similar types of receptors in the patient's larynx.

3. A method according to claim 1, wherein step (a) comprises causing said patient to inhale an aerosol containing tartrate mixed with saline.

4. A method according to claim 1, wherein step (a) comprises causing said patient to inhale an aerosol containing respectively different stimulant strengths of a chemical that is effective to stimulate a sensory innervation of said patient's larynx.

5. A method according to claim 1, wherein step (a) comprises causing said patient to successively inhale an aerosol containing respectively increasing concentrations of a chemostimulant that is effective to stimulate a sensory innervation of said patient's larynx.

6. A method according to claim 5, wherein said chemostimulant is a saline solution of tartrate.

7. A method according to claim 5, wherein step (b) comprises grading the cough of said patient as either a low pneumonia risk if said patient's cough appears normal in response to the initial aerosol spray, or a high pneumonia risk where said patient has a decreased or weak cough in response to the initial concentration spray or requires a more concentrated aerosol application.

8. A method according to claim 5, wherein, during successive stimulant inhalations of said chemostimulant, said patient receives progressively increasing concentrations of the aerosol by tidal breathing at prescribed time intervals.

9. A method according to claim 1, wherein said patient has been intubated in the course of said surgical procedure, and wherein step (a) comprises causing said patient, who has been extubated subsequent to said surgical procedure, to inhale said aerosol that is effective to stimulate said sensory innervation of said normally functional patient's larynx, causing said patient to cough.

* * * * *